(12) United States Patent
Smith et al.

(10) Patent No.: US 11,583,252 B2
(45) Date of Patent: Feb. 21, 2023

(54) MINIATURE TRANSDUCER DEVICE AND RELATED METHODS

(71) Applicant: Arizona Board of Regents on behalf of Arizona State University, Scottsdale, AZ (US)

(72) Inventors: Barbara Smith, Scottsdale, AZ (US); Christopher Miranda, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 1221 days.

(21) Appl. No.: 16/059,699

(22) Filed: Aug. 9, 2018

(65) Prior Publication Data
US 2019/0046159 A1    Feb. 14, 2019

Related U.S. Application Data

(60) Provisional application No. 62/544,286, filed on Aug. 11, 2017.

(51) Int. Cl.
*A61B 8/12* (2006.01)
*A61B 8/00* (2006.01)
*A61B 5/00* (2006.01)

(52) U.S. Cl.
CPC .......... *A61B 8/4483* (2013.01); *A61B 5/0095* (2013.01); *A61B 5/6847* (2013.01); *A61B 8/12* (2013.01); *A61B 8/4416* (2013.01); *A61B 8/445* (2013.01)

(58) Field of Classification Search
None
See application file for complete search history.

(56) References Cited

U.S. PATENT DOCUMENTS

| | | | |
|---|---|---|---|
| 2,761,077 A | 8/1956 | Harris | |
| 5,226,422 A * | 7/1993 | McKeighen | ............. A61B 8/12 600/463 |
| 5,769,086 A | 6/1998 | Ritchart et al. | |
| 5,916,210 A | 6/1999 | Winston | |
| 2007/0132846 A1 | 6/2007 | Broad | |
| 2008/0064921 A1 | 3/2008 | Larkin et al. | |

(Continued)

OTHER PUBLICATIONS

Yang, J-M. et al., "Simultaneous functional photoacoustic and ultrasonic endoscopy of internal organs in vivo", Nature Medicine, Aug. 2012, vol. 18, No. 8, pp. 1297-1302 <DOI:10.1038/nm.2823>.

(Continued)

*Primary Examiner* — Colin T. Sakamoto
(74) *Attorney, Agent, or Firm* — Riverside Law LLP (57) ABSTRACT

A device comprises a miniature transducer having an altered backing geometry that can be placed within different casing sizes of an imaging probe device. The backing geometry extends along a longitudinal axis of the imaging probe and provides an angle (e.g., 45-degree angle) configured to reflect ultrasound and/or light waves/signals in a direction perpendicular to the longitudinal axis of the imaging probe. This design is configured to enable ultrasound and/or light waves/signals to be redirected and dampened within the transducer to preserve a suitable signal to noise ratio while minimizing the required depth of the backing.

9 Claims, 6 Drawing Sheets

(56) References Cited

U.S. PATENT DOCUMENTS

| | | | |
|---|---|---|---|
| 2008/0091104 | A1 | 4/2008 | Abraham |
| 2008/0312561 | A1 | 12/2008 | Chauhan |
| 2009/0048515 | A1 | 2/2009 | Suri et al. |
| 2011/0098572 | A1 | 4/2011 | Chen et al. |
| 2016/0058414 | A1* | 3/2016 | Corl .................. A61B 8/12 600/463 |
| 2017/0367682 | A1 | 12/2017 | Smith et al. |
| 2018/0008243 | A1 | 1/2018 | Irisawa et al. |
| 2018/0078235 | A1 | 3/2018 | Irisawa |
| 2018/0177408 | A1 | 6/2018 | Irisawa et al. |
| 2018/0177409 | A1 | 6/2018 | Irisawa et al. |
| 2019/0110691 | A1 | 4/2019 | Smith et al. |
| 2019/0282069 | A1 | 9/2019 | Smith et al. |

OTHER PUBLICATIONS

Yang, J-M. et al., "Three-dimensional photoacoustic endoscopic imaging of the rabbit esophagus", PLoS ONE, Apr. 2015, vol. 10, No. 4, article e0120269, 15 pages <DOI:10.1371/journal.pone. 0120269>.

Yang, J-M. et al., "Volumetric photoacoustic endoscopy of upper gastrointestinal tract: ultrasonic transducer technology development", Photons Plus Ultrasound: Imaging and Sensing, Feb. 2011, vol. 7899, article 78990D, 7 pages <DOI:10.1117/12.875377>.

Yao, J. et al., "Label-free oxygen-metabolic photoacoustic microscopy in vivo", Journal of Biomedical Optics, Jul. 2011, vol. 16, No. 7, article 076003, 12 pages <DOI:10.1117/1.3594786>.

Yeh, C. et al., "Microvascular quantification based on contour-scanning photoacoustic microscopy", Journal of Biomedical Optics, Sep. 2014, vol. 19, No. 9, article 096011, 6 pages <DOI:10.1117/1.JBO.19.9.096011>.

Zhang, E. et al., "A miniature all-optical photoacoustic imaging probe", Photons Plus Ultrasound: Imaging and Sensing, Feb. 2011, vol. 7899, No. 78991F, 6 pages <DOI:10.1117/12.874883>.

Zhang, E. et al., "In vivo high-resolution 3D photoacoustic imaging of superficial vascular anatomy", Physics in Medicine & Biology, Jan. 2009, vol. 54, No. 4, pp. 1035-1046 <DOI:10.1088/0031-9155/54/4/014>.

Aguirre, A. et al., "Potential Role of Coregistered Photoacoustic and Ultrasound Imaging in Ovarian Cancer Detection and Characterization", Translational Oncology, Feb. 2011 (available online Mar. 2014), vol. 4, No. 1, pp. 29-37 <DOI:10.1593/tlo.10187>.

Alcázar, J. et al., "Endometrial blood flow mapping using transvaginal power Doppler sonography in women with postmenopausal bleeding and thickened endometrium", Ultrasound in Obstetrice and Gynecology, Jun. 2003, vol. 21, No. 6, pp. 583-588 <DOI:10.1002/uog.143>.

Alcázar, .J et al., "Intratumoral Blood Flow Analysis in Endometrial Carcinoma: Correlation with Tumor Characteristics and Risk for Recurrence", Gynecologic Oncology, Feb. 2002 (available online May 2002), vol. 84, No. 2, pp. 258-262 <DOI:10.1006/gyno.2001.6496>.

Alcázar, J. et al., "Three-dimensional power Doppler ultrasound scanning for the prediction of endometrial cancer in women with postmenopausal bleeding and thickened endometrium", American Journal of Obstetrics and Gynecology, Jan. 2009 (available online Oct. 2008), vol. 200, No. 1, pp. 44.e1-44.e6 <DOI:10.1016/j.ajog.2008.08.027>.

Alcázar, J. et al., "Three-dimensional ultrasound for assessing women with gynecological cancer: a systematic review", Gynecologic Oncology, Mar. 2011 (available online Nov. 2010), vol. 120, No. 3, pp. 340-346 <DOI:10.1016/j.ygyno.2010.10.023>.

Amant, F. et al., "Endometrial Cancer", The Lancet, Aug. 2005, vol. 366, No. 9484, pp. 491-505 <DOI:10.1016/S0140-6736(05)67063-8>.

Antonsen, S. et al., "MRI, PET/CT and ultrasound in the preoperative staging of endometrial cancer—A multicenter prospective comparative study", Gynecologic Oncology, Feb. 2013 (available online Nov. 2013), vol. 128, No. 2, pp. 300-308 <DOI:10.1016/j.ygyno.2012.11.025>.

Bai, X. et al., "Intravascular optical-resolution photoacoustic tomography with a 1.1 mm diameter catheter", PLoS ONE, Mar. 2014, vol. 9, No. 3, article e92463, 6 pages <DOI:10.1371/journal.pone.0092463>.

Bedner, R. et al., "Hysteroscopy with directed biopsy versus dilatation and curettage for the diagnosis of endometrial hyperplasia and cancer in perimenopausal women", European Journal of Gynaecological Oncology, 2007, vol. 28, No. 5, pp. 400-402.

Bohndiek, S. et al., "Development and Application of Stable Phantoms for the Evaluation of Photoacoustic Imaging Instruments", PLoS ONE, Sep. 2013, vol. 8, No. 9, article e75533, 14 pages <DOI:10.1371/journal.pone.0075533>.

Burke, W. et al., "Endometrial cancer: a review and current management strategies: part II", Gynecologic Oncology, Aug. 2014 (available online Jun. 2014), vol. 134, No. 2, pp. 393-402 <DOI:10 1016/j.ygyno.2014.06.003>.

Cheng, W-F. et al., "Clinical application of intratumoral blood flow study in patients with endometrial carcinoma", Cancer, 1998 (available online Oct. 2000), vol. 82, No. 10, pp. 1881-1886 <DOI:10.1002/(SICI)1097-0142 (19980515)82:10<1881 ::AID-CNCR10>3.0.CO;2-P>.

Clement, P., "The pathology of uterine smooth muscle tumors and mixed endometrial stromal-smooth muscle tumors: a selective review with emphasis on recent advances", International Journal of Gynecological Pathology, Jan. 2000, vol. 19, No. 1, pp. 39-55.

Emoto, M. et al., "Clinical usefulness of color Doppler ultrasound in patients with endometrial hyperplasia and carcinoma", Cancer,Feb. 2002 (available online Jan. 2002), vol. 94, No. 3, pp. 700-706 <DOI:10.1002/cncr.10208>.

Goldstein, S., "The role of transvaginal ultrasound or endometrial biopsy in the evaluation of the menopausal endometrium", American Journal of Obstetrics and Gynecology, Jul. 2009, vol. 201, No. 1, pp. 5-11 <DOI:10.1016/j.ajog.2009.02.006>.

Jansen, K. et al., "Lipid detection in atherosclerotic human coronaries by spectroscopic intravascular photoacoustic imaging", Optics Express, Sep. 2013, vol. 21, No. 18, pp. 21472-21484 <DOI:10.1364/OE.21.021472>.

Jathoul, A. et al., "Deep in vivo photoacoustic imaging of mammalian tissues using a tyrosinase-based genetic reporter", Nature Photonics, Apr. 2015 (available online Mar. 2015), vol. 9, No. 4, pp. 239-246 <DOI:10.1038/hphoton.2015.22>.

Karpiouk, A. et al., "Feasibility of in vivo intravascular photoacoustic imaging using integrated ultrasound and photoacoustic imaging catheter", Journal of Biomedical Optics, Sep. 2012, vol. 17, No. 9, article 096008, 7 pages <DOI:10.1117/1.JBO.17.9.096008>.

Eshavarzi, A. et al., "Attenuation coefficient and sound speed in human myometrium and uterine fibroid tumors", Journal of Ultrasound in Medicine, May 2001, vol. 20, No. 5, pp. 473-480 <DOI:10.7863/jum.2001.20.5.473>.

Kim, C. et al., "In Vivo Molecular Photoacoustic Tomography of Melanomas Targeted by Bioconjugated Gold Nanocages", ACS Nano, Aug. 2010 (available online Jul. 2010), vol. 4, No. 8, pp. 4559-4564 <DOI:10.1021/nn100736c>.

Kodama, J. et al., "Correlation of presenting symptoms and patient characteristics with endometrial cancer prognosis in Japanese women", International Journal of Gynecology and Obstetrics, Sep. 2005, vol. 91, No. 2, pp. 151-156 <DOI: 10.1016/j.ijgo.2005.08.002>.

Kruger, R. et al., "Dedicated 3D photoacoustic breast imaging", Medical Physics, Nov. 2013 (available online Oct. 2013), vol. 40, No. 11, article 113301, 8 pages <DOI:10.1118/1.4824317>.

Lao, Y. et al., "Noninvasive photoacoustic imaging of the developing vasculature during early tumor growth", Physics in Medicine & Biology, Jul. 2008, vol. 53, No. 15, pp. 4203-4212 <DOI:10.1088/0031-9155/53/15/013>.

Lee, C-N. et al., "Angiogenesis of endometrial carcinomas assessed by measurement of inlrafumoral blood flow, microvessel density, and vascular endothelial growth factor levels", Obstetrics & Gynecology, Oct. 2000 (available online Sep. 2000), vol. 96, No. 4, pp. 615-621 <DOI:10.1016/S0029-7844(00)00976-5>.

(56) References Cited

OTHER PUBLICATIONS

Li, M-L. et al., "Simultaneous Molecular and Hypoxia Imaging of Brain Tumors In Vivo Using Spectroscopic Photoacoustic Tomography", Proceedings of the IEEE, Mar. 2008 (available online Feb. 2008), vol. 96, No. 3, pp. 481-489 <DOI:10.1109/JPROC.2007.913515>.

Mallidi, S. et al., "Photoacoustic imaging in cancer detection, diagnosis, and treatment guidance", Trends in Biotechnology, May 2011 (available online Feb. 2011), vol. 29, No. 5, pp. 213-221 <DOI:10.1016/j.tibtech.2011.01.006>.

Merz, E. et al., "Sonographic size of uterus and ovaries in pre- and postmenopausal women", Ultrasound in Obstetrics and Gynecology, Jan. 1996, vol. 7, No. 1, pp. 38-42 <DOI:10.1046/j.1469-0705.1996.07010038.x>.

Miranda, C. et al., "Intrauterine photoacoustic and ultrasound imaging probe, journal of biomedical optics", Journal of Biomedical Optics, Apr. 2018, vol. 23, No. 4, article 046008, 9 pages <DOI:10.1117/1.JBO.23.4.046008>.

Morice, P. et al., "Endometrial Cancer", The Lancet, Mar. 2016 (published Sep. 2015), vol. 387, No. 10023, pp. 1094-1108 <DOI:10.1016/S0140-6736(15)00130-0>.

Nicholson, W. et al., "Patterns of ambulatory care use for gynecologic conditions: A national study", American Journal of Obstetrics and Gynecology, Mar. 2001 (available online May 2002), vol. 184, No. 4, pp. 523-530 <DOI:10.1067/mob.2001.111795>.

Ning, B. et al., "Simultaneous photoacoustic microscopy of microvascular anatomy, oxygen saturation, and blood flow", Optics Letters, Mar. 2015, vol. 40, No. 6, pp. 910-913 <DOI:10.1364/OL.40.000910>.

Ribatti, D. et al., "Neovascularization and mast cells with tryptase activity increase simultaneously with pathologic progression in human endometrial cancer", American Journal of Obstetrics and Gynecology, Dec. 2005, vol. 193, No. 6, pp. 1961-1965 <DOI:10.1016/j.ajog.2005.04.055>.

Salvesen, H. et al., "Independent prognostic importance of microvessel density in endometrial carcinoma", British Journal of Cancer, Apr. 1998, vol. 77, No. 7, pp. 1140-1144.

Schwarz, M. et al., "Three-dimensional multispectral optoacoustic mesoscopy reveals melanin and blood oxygenation in human skin in vivo", Journal of Biophotonics, Jan. 2016 (available online Nov. 2015), vol. 9, No. 1-2, pp. 55-60 <DOI:10.1002/jbio.201500247>.

Sethuraman, S. et al., "Intravascular photoacoustic imaging using an IVUS imaging catheter", IEEE Transactions on Ultrasonics, Ferroelectrics, and Frequency Control, May 2007 (date of publication Jun. 2007), vol. 54, No. 5, pp. 978-986 <DOI:10.1109/TUFFC.2007.343>.

Siegel, R. et al., "Cancer statistics, 2016", CA: A Cancer Journal for Clinicians, Jan./Feb. 2016, vol. 66, No. 1, pp. 7-30 <DOI:10.3322/caac.21332>.

Siphanto, R. et al., "Serial noninvasive photoacoustic imaging of neovascularization in tumor angiogenesis", Optics Express, Jan. 2005, vol. 13, No. 1, pp. 89-95 <DOI:10.1364/OPEX.13.000089>.

Smith-Bindman, R. et al., "Endovaginal Ultrasound to Exclude Endometrial Cancer and Other Endometrial Abnormalities", JAMA, Nov. 1998, vol. 280, No. 17, pp. 1510-1517 <DOI:10.1001/jama.280.17.1510>.

Stewart, E., "Uterine fibroids", The Lancet, Jan. 2001, vol. 357, No. 9252, pp. 293-298 <DOI:10.1016/S0140-6736(00)03622-9>.

Symonds, I. et al., "Ultrasound, hysteroscopy and endometrial biopsy in the investigation of endometrial cancer", Best Practice & Research Clinical Obstetrics & Gynaecology, Jun. 2001 (available online May 2002), vol. 15, No. 3, pp. 381-391 <DOI:10.1053/beog.2000.0183>.

Tamai, K. et al., "Diffusion-weighted MR imaging of uterine endometrial cancer", Journal of Magnetic Resonance Imaging, Aug. 2007, vol. 26, No. 3, pp. 682-687 <DOI:10.1002/jmri.20997>.

Timmermans, A. et al., "Endometrial Thickness Measurement for Detecting Endometrial Cancer in Women With Postmenopausal Bleeding: A Systematic Review and Meta-Analysis", Obstetrics & Gynecology, Jul. 2010, vol. 116, No. 1, pp. 160-167 <DOI:10.1097/AOG.0b013e3181e3e7e8>.

Wang, B. et al., "Intravascular photoacoustic imaging of lipid in atherosclerotic plaques in the presence of luminal bood", Optics Letters, Apr. 2012, vol. 37, No. 7, pp. 1244-1246 <DOI:10.1364/OL.37.001244>.

Wang, B. et al., "Intravascular Photoacoustic Imaging", IEEE Journal of Selected Topics in Quantum Electronics, May-Jun. 2010 (date of publication Mar. 2010), vol. 16, No. 3, pp. 588-599 <DOI:10.1109/JSTQE.2009.2037023>.

Wang, L. et al., "Photoacoustic Tomography: In Vivo Imaging from Organelles to Organs", Science, Mar. 2012, vol. 335, No. 6075, pp. 1458-1462.

Wang, P. et al., "High-speed Intravascular Photoacoustic Imaging of Lipid-laden Atherosclerotic Plaque Enabled by a 2-kHz Barium Nitrite Raman Laser", Scientific Reports, Nov. 2014, vol. 4, No. 6889, 7 pages <DOI:10.1038/srep06889>.

Wang, X. et al., "Noninvasive imaging of hemoglobin concentration and oxygenation in the rat brain using high-resolution photoacoustic tomography", Journal of Biomedical Optics, Mar./Apr. 2006, vol. 11, No. 2, article 024015, 9 pages <DOI:10.1117/1.2192804>.

Wright, J. et al., "Contemporary management of endometrial cancer", The Lancet, Apr. 2012 (published Mar. 2012), vol. 379, No. 9823, pp. 1352-1360 <DOI:10.1016/S0140-6736(12)60442-5>.

Xu, M. et al., "Photoacoustic imaging in biomedicine", Review of Scientific Instruments, Apr. 2006, vol. 77, article 041101, 22 pages <DOI:10.1063/1.2195024>.

Yang, J-M. et al., "Photoacoustic endoscopy", Optics Letters, May 2009, vol. 34, No. 10, pp. 1591-1593 <DOI:10.1364/OL.34.001591>.

\* cited by examiner

MINIATURE TRANSDUCER DEVICE AND RELATED METHODS

CROSS-REFERENCE TO RELATED APPLICATIONS

The present application claims priority to and incorporates by reference U.S. provisional application 62/544,286, which was filed on Aug. 11, 2017, and entitled Miniature Transducer Device and Related Methods.

BACKGROUND

The present invention relates generally to devices for multimodal imaging and more specifically, but not by way of limitation, to devices and related methods of combined photoacoustic and ultrasound imaging with real-time data processing and image reconstruction that can be miniaturized to fit into a variety of imaging devices.

Traditionally, in the United States, women who enter a clinic with abnormal uterine bleeding—regardless of, shape, color, economic standing, history or ethnicity—are considered to have endometrial cancer, until proven otherwise. Current methods of diagnosis require a combination of imaging and biopsy tests to be performed within a series of multiple clinical visits. Typical diagnostic tests used to rule out endometrial cancer include: i) transvaginal and/or pelvic ultrasound, ii) endometrial biopsy, iii) hysteroscopy, and iv) D&C (Dilation and curettage) testing. This succession of painful, expensive, and time-consuming tests fail to meet the needs of the physician and the patient. For example, transvaginal and/or pelvic ultrasounds, endometrial biopsies, and hysteroscopies may render inconclusive results. D&C testing may be considered invasive. Thus, there remains a need for a system providing more efficient, accurate, and cost-effective imaging and biopsy collection, which may be used in screening for endometrial cancer.

SUMMARY

Embodiments may include imaging systems and/or related methods that can serve to minimize invasiveness of imaging processes. Embodiments may include transducers or other imaging devices scaled and constructed to perform with suitable image quality, such as suitable signal to noise ratios from imaging probes. Embodiments may include a transducer sized and configured to enable miniaturization of probes of an imaging system with suitable imaging specifications and capabilities.

Some embodiments may include at least one transducer configured to redirect and dampen ultrasound waves using a forty-five-degree angle backing that extends perpendicular from a normal of a piezoelectric element. The extended backing may be preferably perpendicular to the normal of the piezoelectric element. In so doing, embodiments may allow for the entire length of the backing to be maintained (thereby providing a reduced signal to noise ratio) while minimizing the required depth of the backing. Embodiments may provide a signal to noise ratio that is comparable or better than conventional transducers while allowing the transducer to fit within a smaller diameter probe or imaging device. Transducers of embodiments may be employed in a variety of new applications including those where size of the transducer is governing or otherwise critical. Transducer designs of embodiments may be used in array arrangements as well as in single element designs. These arrays may be in a single probe, in concurrent multiple probes, in single imaging devices and in multiple concurrent imaging devices. Transducers may be located at the distal end of a probe or imaging device and may be located at other positions as well. For example, at bend positions of a probe or imaging device, at multiple positions along the length of a probe or imaging device, and even as proximal ends of the probe or imaging device. Still further locations of the transducer in embodiments are also possible.

Some embodiments may include a probe such as an endoscope with working distal end that may comprise a cannula or catheter that may extend from the distal end for performing biopsies or other procedures. The endoscope or other probe may include a first end, a second end, and a channel between the first end and the second end, the channel disposed in a longitudinal direction along a longitudinal axis of the cannula; and a transducer disposed within the channel at or near the first end of the probe, the transducer comprising: a housing, a backing, at least one reflective angled surface, and a piezoelectric element, wherein the backing of the transducer extends within the channel in the longitudinal direction along the longitudinal axis of the probe. MEMS technology may be employed in embodiments for positioning the reflective angled surface such that different angles may be employed during a procedure to increase the range of scanning and observation being employed. In some embodiments, the length of backing that extends within the channel in the longitudinal direction along the longitudinal axis of the probe may be equal to or greater than a depth of the backing. The depth of the backing may be substantially equal to an inner diameter of the probe. In some embodiments the piezoelectric element may be disposed within an aperture disposed in a surface of the probe. In some embodiments, the backing may extend within the channel in a direction perpendicular from a normal of the piezoelectric element. In some embodiments the device may include an ultrasound transmission line configured to extend within the channel in the longitudinal direction along the longitudinal axis of the probe between the transducer and the second end of the probe. In some embodiments, the reflective angled surface may be disposed at a 45-degree angle relative to the longitudinal axis of the probe. In some embodiments, the reflective angled surface may be disposed at a 45-degree angle relative to the normal of the piezoelectric element. In some embodiments, the reflective angled surface may be disposed at a boundary between the housing and the backing. The reflective angle may also be set at other angles, such as 15°, 30°, 60°, and 75°. In these instances, a single transducer may be employed or multiple transducers may be employed in the same probe such that a probe may be able to inspect at numerous angles when inserted at a target site. For example, if a 45° and 15° transducer were employed at the distal end of an endoscope or cannula or other probe, monitoring may first be conducted using the 45° transducer and then using the 15° transducer in order to observe different target areas once the probe is positioned without having the need to reposition the probe, or with only needing to rotate the probe once it reaches its target location and position. For example, the probe may rotate as it travels along the axis of the uterus or other target region to develop a 3D image of the region, organ, etc. being scanned and observed.

Some embodiments may include a device including: a cannula having a first end, a second end, and a channel between the first end and the second end, the channel disposed in a longitudinal direction along a longitudinal axis of the cannula; a transducer disposed within the channel at the first end of the cannula, the transducer comprising: a housing, a backing, at least one reflective angled surface, and one or more piezoelectric element(s); and an optical transmission line disposed within the channel at the first end of the cannula, wherein the backing of the transducer and the optical transmission line extend within the channel in the longitudinal direction along the longitudinal axis of the cannula, wherein a portion of the optical transmission line is disposed within a channel of the backing. In some embodiments, the piezoelectric element may comprise an aperture disposed within the piezoelectric element. In some embodiments, a center of the aperture may be located at a normal of the piezoelectric element.

Some embodiments may comprise a system including: a device described in the embodiments herein; a receiver configured to receive a signal from the transducer; an amplifier configured to amplify the signal received by receiver; and a data acquisition system configured to receive a signal from the amplifier. In some embodiments, the system may further include a position control device configured to direct an actuator to move the device to the location of interest. Some embodiments may be configured to capture at least one optical image, a series of optical images, an ultrasound image, and a photoacoustic image. Some embodiments may be configured to capture a mapped image of human tissue, where the mapped image comprises at least one of an optical image, an ultrasound image, and a photoacoustic image. This captured mapped image may include a three-dimensional mapping of at least one of the human tissue and vasculature of an organ comprised by human tissue. Contrast agents may also be sensed in embodiments and photoacoustic analysis techniques may be served by these sensed contrast agents.

Some embodiments may include a method including: generating an ultrasound signal using a device, the device including: a cannula having a first end, a second end, and a channel between the first end and the second end, the channel disposed in a longitudinal direction along a longitudinal axis of the cannula; and a transducer disposed within the channel at the first end of the cannula, the transducer comprising: a housing, a backing, at least one reflective angled surface, and a piezoelectric element, wherein the backing of the transducer extends within the channel in the longitudinal direction along the longitudinal axis of the cannula, emitting the ultrasound signal in a longitudinal direction; reflecting the ultrasound signal off of the reflective angled surface; and emitting the ultrasound signal in a direction perpendicular to the longitudinal direction and parallel to a normal of the piezoelectric element. In some embodiments, methods may further comprise: receiving an ultrasound return signal by the transducer in the direction perpendicular to the longitudinal direction and parallel to the normal of the piezoelectric element in response to emitting the ultrasound signal; reflecting the ultrasound return signal off of the reflective angled surface; and emitting the ultrasound return signal in the longitudinal direction. In some embodiments, methods may further comprise: generating an optical signal using an optical transmission line; emitting the optical signal in the longitudinal direction; reflecting the optical signal off of the reflective angled surface; and emitting the optical signal through an aperture disposed in the piezoelectric element in the direction perpendicular to the longitudinal direction and parallel to the normal of the piezoelectric element. In some embodiments, methods may further comprise: receiving a photoacoustic signal by the transducer in the direction perpendicular to the longitudinal direction and parallel to the normal of the piezoelectric element in response to emitting the optical signal; reflecting the return vibration signal off of the reflective angled surface; and emitting the return vibration signal in the longitudinal direction. In some embodiments, methods may further comprise: forming an image of human tissue in real time based on the received ultrasound return signal and/or the photoacoustic signal.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with embodiments are described above and others are described below and each may be combined in various ways regardless of whether provided above or below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
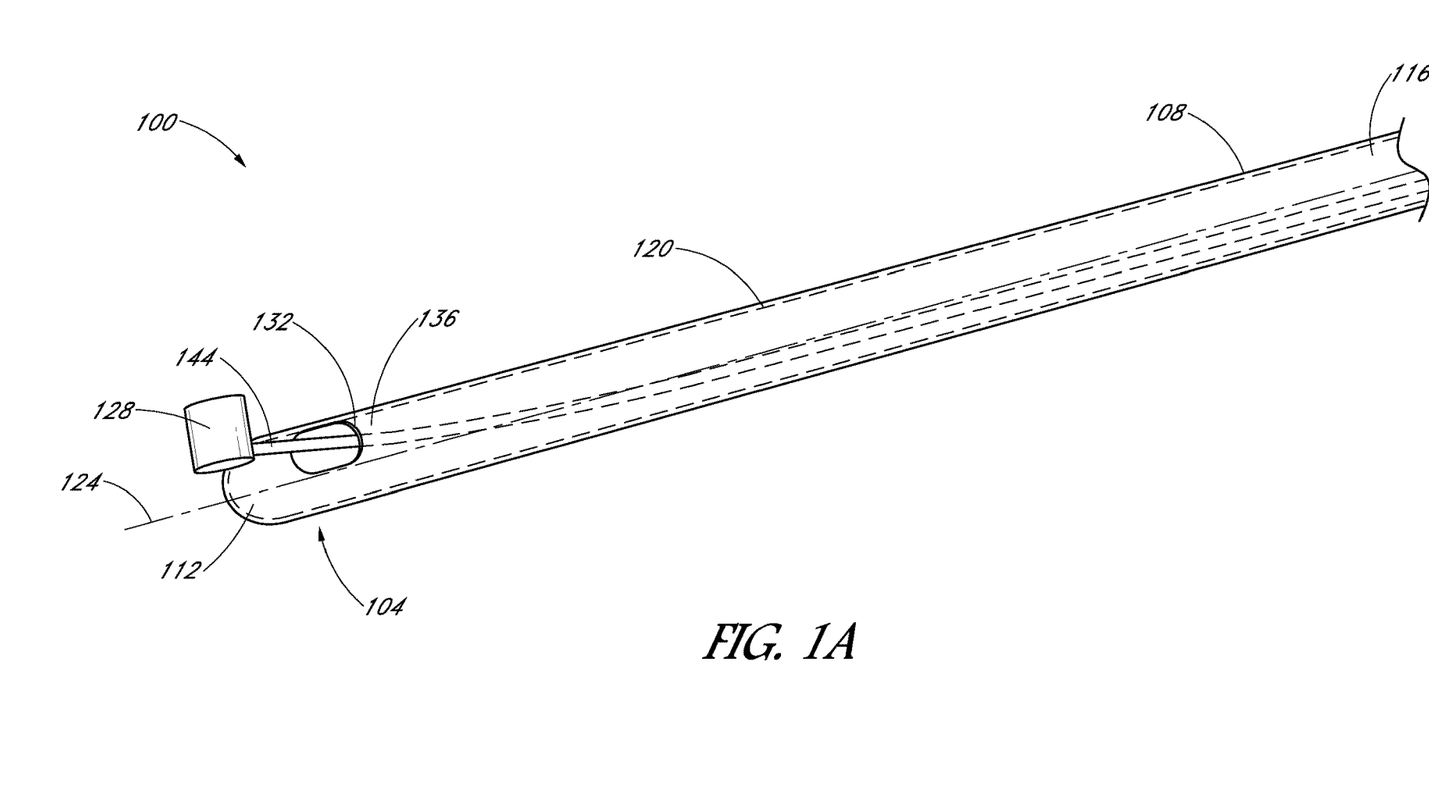
FIGS. 1A-1C depict an imaging probe and transducer of an imaging system as may be employed or modified in embodiments.
Figure 1B:
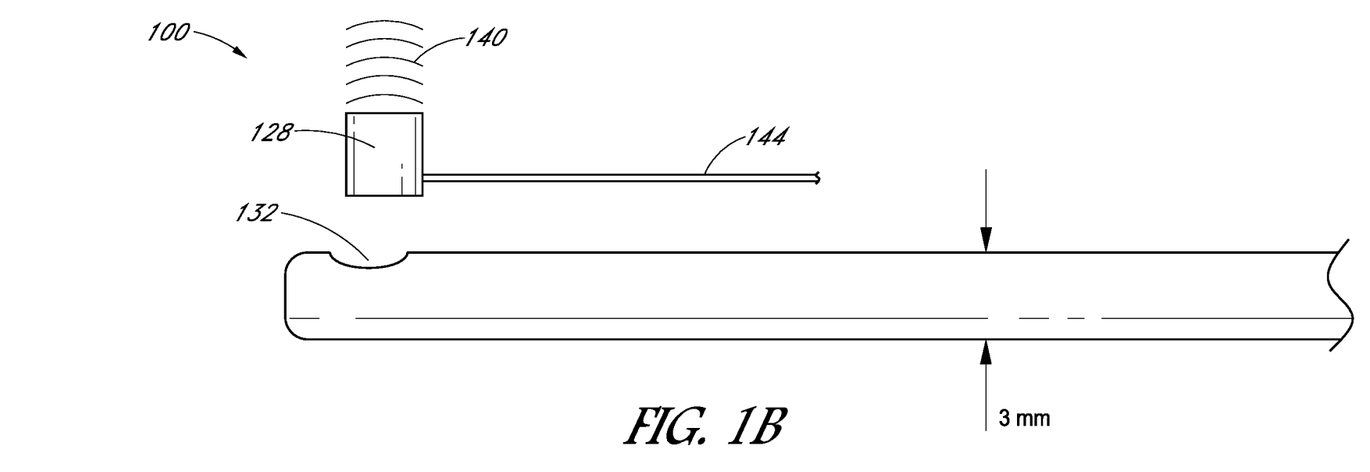
Figure 1C:
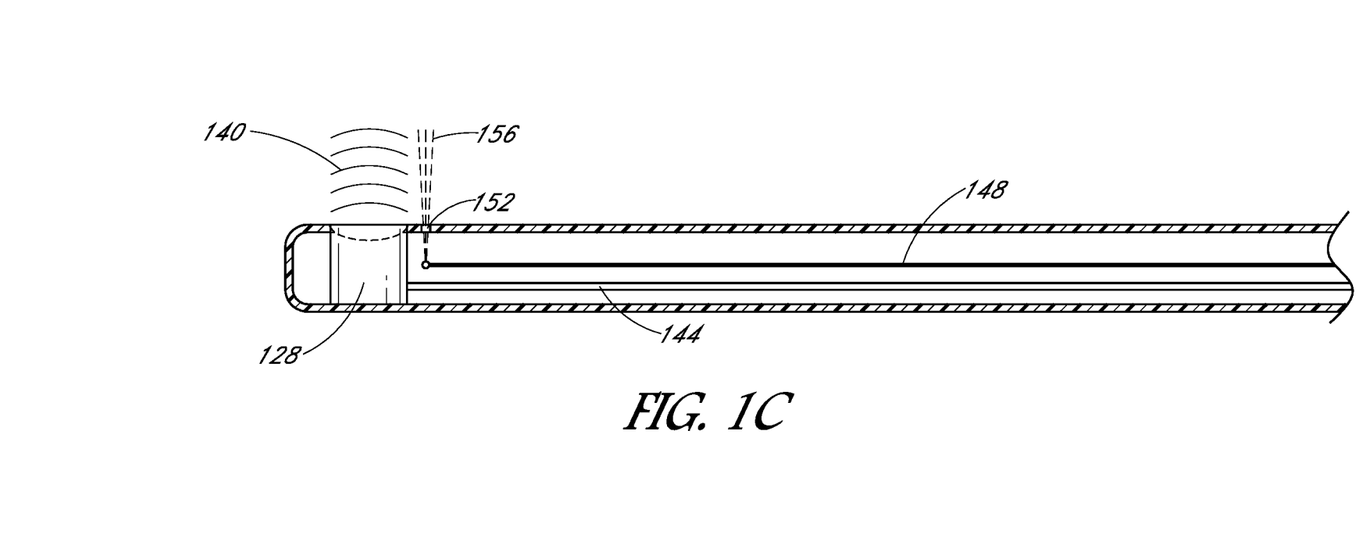

Referring now to the drawings, and more specifically to FIGS. 1A-C, shown therein and designated by the reference numeral 100 is one embodiment of the present systems. In the embodiment shown, system 100 includes an insertion device 104. In this embodiment, insertion device 104 may be a biomedical device for screening for (e.g., endometrial) cancer by way of imaging and controlled biopsy sample collection.

In the depicted embodiment, insertion device 104 comprises a flexible cannula 108 (e.g., a flexible catheter) having a first end 112, a second end 116, and a channel 120 extending between the first end and the second end. In this embodiment, cannula 108 may be characterized by and described relative to a longitudinal axis 124 extending along a length of the cannula. In the embodiment shown, cannula 108 is 3 mm wide. In the embodiment shown, cannula 108 may be coupled to a transducer 128 at first end 112 of the cannula. In some embodiments (e.g., 100), a cannula (e.g., 108) and a transducer (e.g., 128) may be integrally formed and/or the transducer may be disposed at any position along the cannula between a first end (e.g., 112) and a second end (e.g., 116) of the cannula. In some embodiments, second end 116 of cannula 108 may be coupled to an actuator (not shown) that can include a rotary motor and a linear actuator. In some embodiments, the rotary motor may be actuatable to move (e.g., rotate) insertion device 104 about longitudinal axis 124 and the linear actuator may be actuatable to move the insertion device axially relative to the longitudinal axis. In some embodiments, insertion device 104 may rotate about longitudinal axis 124 for 360 degrees. In some embodiments, the actuator may be configured to be (e.g., electronically) coupled to a position control device configured to control the rotational and/or linear velocity, acceleration, and/or position of insertion device 104 relative to the tissue of an organ of a patient. More specifically, the position control device may be configured to send respective (e.g., electronic) signals to the rotary motor and/or linear actuator to control the velocity, acceleration, position, and/or the like of insertion device 104.

In the depicted embodiment, insertion device 104 may include a transducer aperture 132 defined by an outer circumferential surface 136 of the insertion device. In some embodiments, transducer 128 may be an ultrasound transducer. In this embodiment, transducer 128 may be configured to emit an ultrasound signal 140 radially outward (e.g., relative to longitudinal axis 124) through transducer aperture 132. More specifically, in the depicted embodiment, transducer 128 may be configured to emit ultrasound signal 140 in a direction substantially perpendicular relative to longitudinal axis 124. In the embodiment shown, insertion device 104 may include an ultrasound transmission line 144 configured to transmit a (e.g., electronic) signal between transducer 128 and an ultrasound pulser-receiver (not shown). As shown, at least a portion of ultrasound transmission line 124 may extend within channel 120 of cannula 108. In some embodiments, an ultrasound pulser-receiver may be coupled to an amplifier configured to amplify an electronic signal received by the pulser-receiver from transducer 128. In some embodiments, a system (e.g., 100) may include a pulser and a receiver as separate components.

In the embodiment shown in FIG. 1C, insertion device 104 may include a light transmission line 148 configured to transmit light from a fiber optic alignment stage to at least one reflective surface, such as, for example, one or more mirrors. As shown, at least a portion of light transmission line 148 may extend within channel 120 of cannula 108. In this embodiment, light transmission line 148 comprises a fiber optic cable. In some embodiments such as that shown in FIG. 1A, ultrasound transmission line 124 and light transmission line 148 can be disposed together in a single line. In other embodiments such as that shown in FIG. 1C, ultrasound transmission line 124 and light transmission line 148 can be disposed as separate lines. In some embodiments, at least one reflective surface may be disposed in insertion device 104 such that the reflective surface is configured to direct light through a light aperture 152 defined by the insertion device 104. More particularly, a reflective surface may comprise a right-angle mirror configured to direct a light signal in a direction substantially perpendicular to longitudinal axis 124. In some embodiments, a reflective surface may be coupled to one or more adjustable rail(s) configured to adjust the position of the reflective surface in insertion device 104 such that the reflective surface reflects a light signal through light aperture 152 (e.g., in a direction substantially parallel relative to an ultrasound signal). For example, in the embodiment shown in FIG. 1C, ultrasound signal 140 emitted by transducer 128 and light signal 156 transmitted by light transmission line 148 may be configured to be emitted in a direction substantially parallel relative to each other. More specifically, in the embodiment shown, transducer aperture 132 and light aperture 152 may be configured to be substantially longitudinally aligned in insertion device 104.

In some embodiments, insertion device 104 may include a biopsy device (not shown) removably insertable in cannula 108 and configured to collect a tissue sample from an organ of a patient. In this embodiment, a biopsy device comprises a biopsy pipelle. In other embodiments, a biopsy device may include any other suitable device configured to collect and/or examine tissue from a patient, such as, for example, a Novak curette and/or the like. In some embodiments, a biopsy device may be at least partially disposed in channel 120 of cannula 108 and may include an aperture (e.g., at an end of the biopsy device). In this embodiment, the end of the biopsy device may be axially and/or laterally movable relative to longitudinal axis 124 such that the biopsy device may be properly positioned in a patient. In some embodiments, for example, a biopsy device may be configured to provide a suction force at an aperture of insertion device 104 in an effort to collect a sample of tissue from a patient.

In some embodiments, system 100 may include a data acquisition system (not shown). In some embodiments, a data acquisition system may include a data acquisition device and a trigger. In some embodiments, a data acquisition device may be configured to receive an amplified (e.g., electronic) signal from an amplifier and transmit image data to a computer having a display, at least one processor, and memory. More specifically, a data acquisition device may be configured to collect quantitative data from a pulser-receiver and transmit quantitative data to a computer for further processing. In some embodiments, a computer may be configured to construct and/or reconstruct a three-dimensional image (e.g., map) representing the (e.g., soft) tissue and/or vasculature surrounding insertion device 104 in real time based on the quantitative data received from a data acquisition device. In this way and others, system 100 can provide a real-time three-dimensional mapping (e.g., a twodimensional image of a three-dimensional volume) of an organ from inside the organ. In some embodiments, a computer may include a physician-guided software program (e.g., an algorithm) configured to identify tissue regions of interest, such as, for example, lesions on endometrium tissue.

In some embodiments, a data acquisition system may be coupled to a position control device and configured to transmit a (e.g., electronic) signal to the position control device thereby directing the rotational and linear movement of insertion device 104 via the position control device. In some embodiments, a trigger of data acquisition system may be coupled to a laser and configured to actuate the laser between an on and off state. In some embodiments, a laser may comprise a near-infrared laser. Embodiments may be fully, partially and manually operated. A medical technician may control movement of the probe and the transducer or other components manually, semi-automatically, and completely automatically. When manually controlled, a medical technician may control all aspects of the probe as the procedure is performed. When semi-automatically operated some portions of the procedure may be manually performed while other portions may be automatically controlled. For example, the probe may be positioned by the technician while control of the position of the transducer within the probe or when pictures or other scanning takes place, may be automatically controlled. When in full automatic mode al features and aspects of the procedure may selected beforehand by the technician but may be carried out under autonomous control once the procedure begins.

Figure 2:
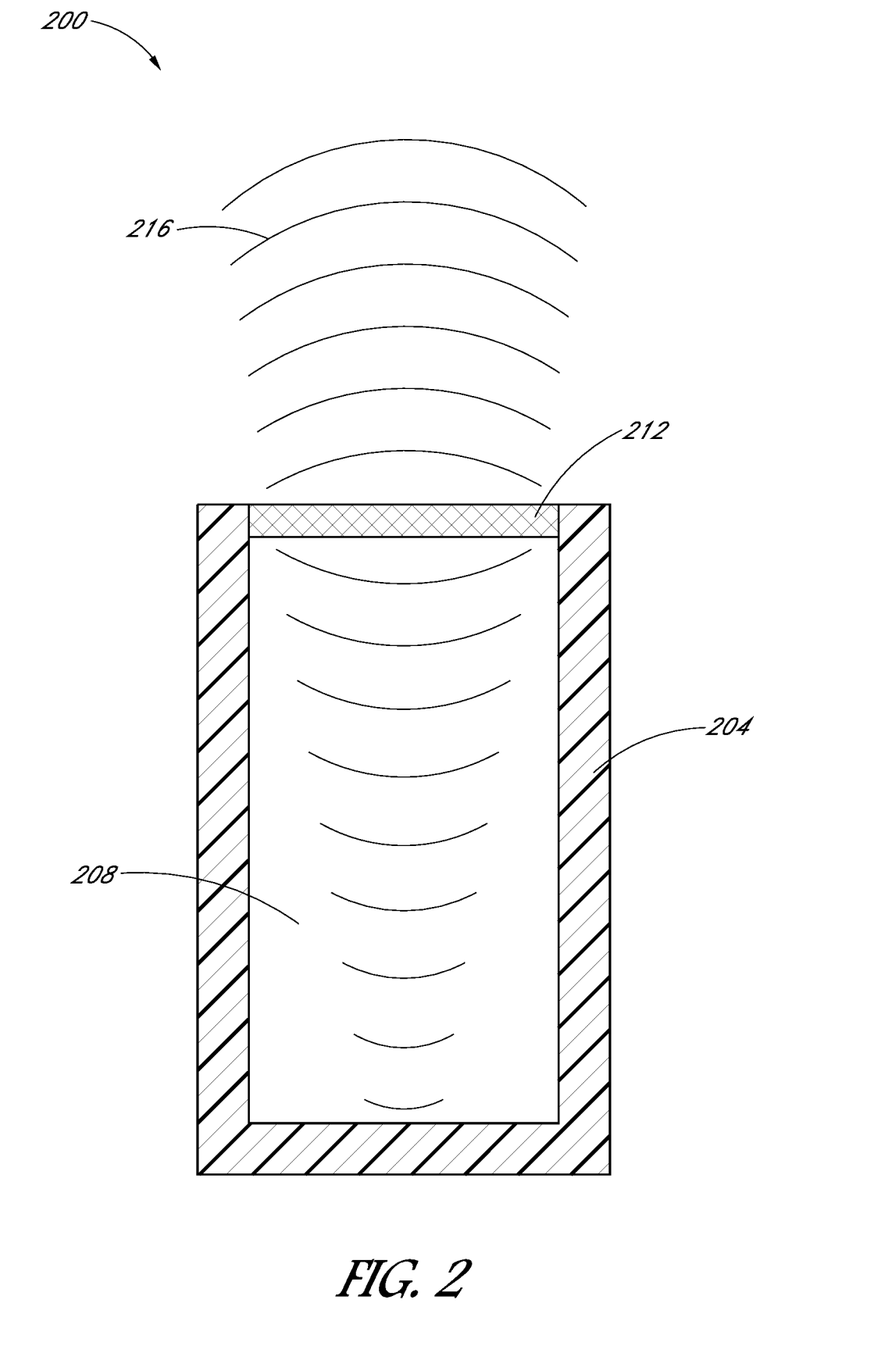
FIG. 2 depicts components of a transducer of an imaging system as may be employed or modified in embodiments.

FIG. 2 depicts a transducer 200 of an imaging system. In some embodiments, transducer 200 can be used as transducer 128 shown in FIGS. 1A-C. In the embodiment shown, transducer 200 includes a housing 204, a backing 208, and at least one piezoelectric element 212 such as a crystal or ceramic element. In some embodiments, housing 204 can include an acoustic insulating layer that can help isolate ultrasound signals 216 from noise. In the embodiment shown, backing 208 is comprised of a dampening material that damps the ultrasound signals and reduces signal noise from the generated signal. In the embodiment shown, ultrasound signals 216 pass through backing 208 and vibrate piezoelectric element 212 which then converts the vibrations into electrical signals. As piezoelectric element 212 vibrates, sound waves are absorbed by backing 208 which damps the ultrasound signals 216 and minimizes the noise associated with the sound generated. The size and/or amount of backing 208 is important in order to minimize the noise associated with the sound generated. The less backing material backing 208 includes, the more noise results due to sound waves reverberating and returning back to contact piezoelectric element 212. Thus, the amount of noise is directly related to both the backing as well as the frequency of the sound. In the embodiment shown, backing 208 is about 3 mm in outer diameter or the same size as a width (or inner diameter) of cannula 108.

Figure 3A:
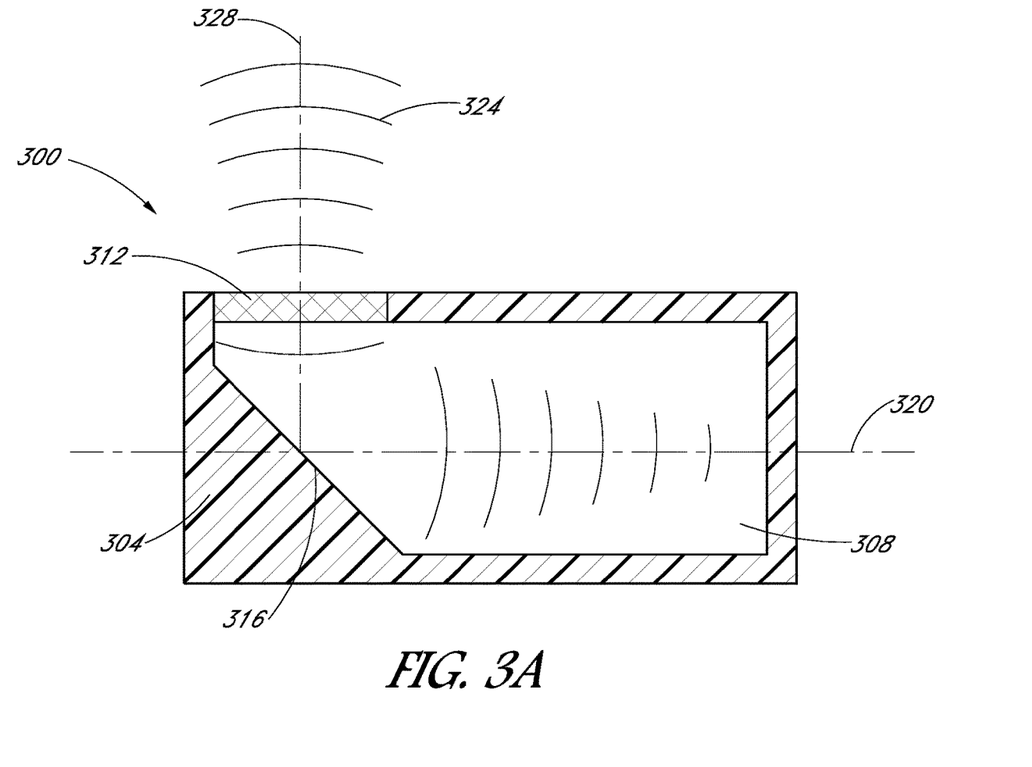
FIGS. 3A-3C depict a miniaturized transducer as may be employed or modified in embodiments.
Figure 3B:
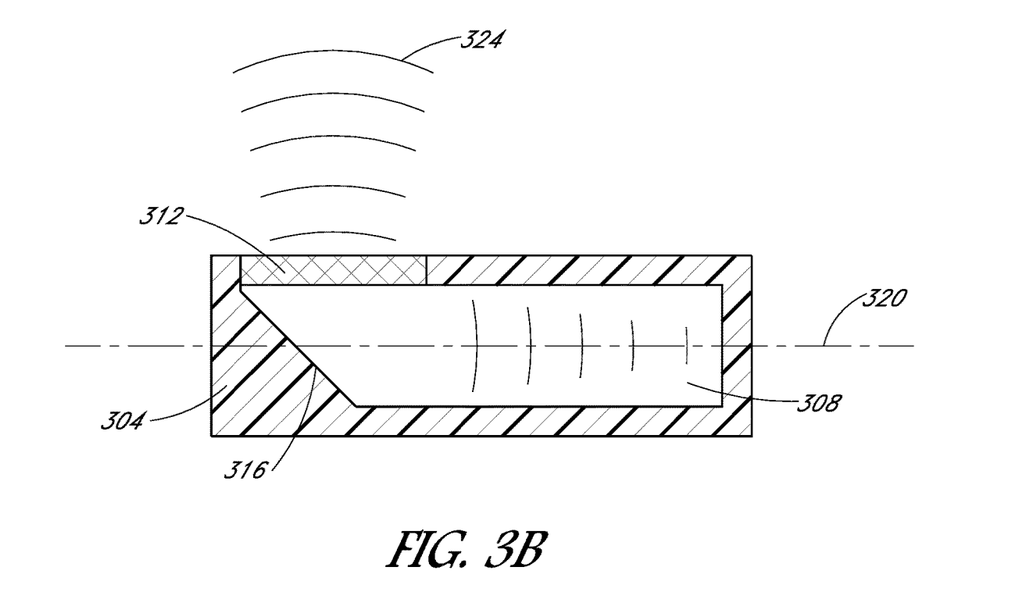
Figure 3C:
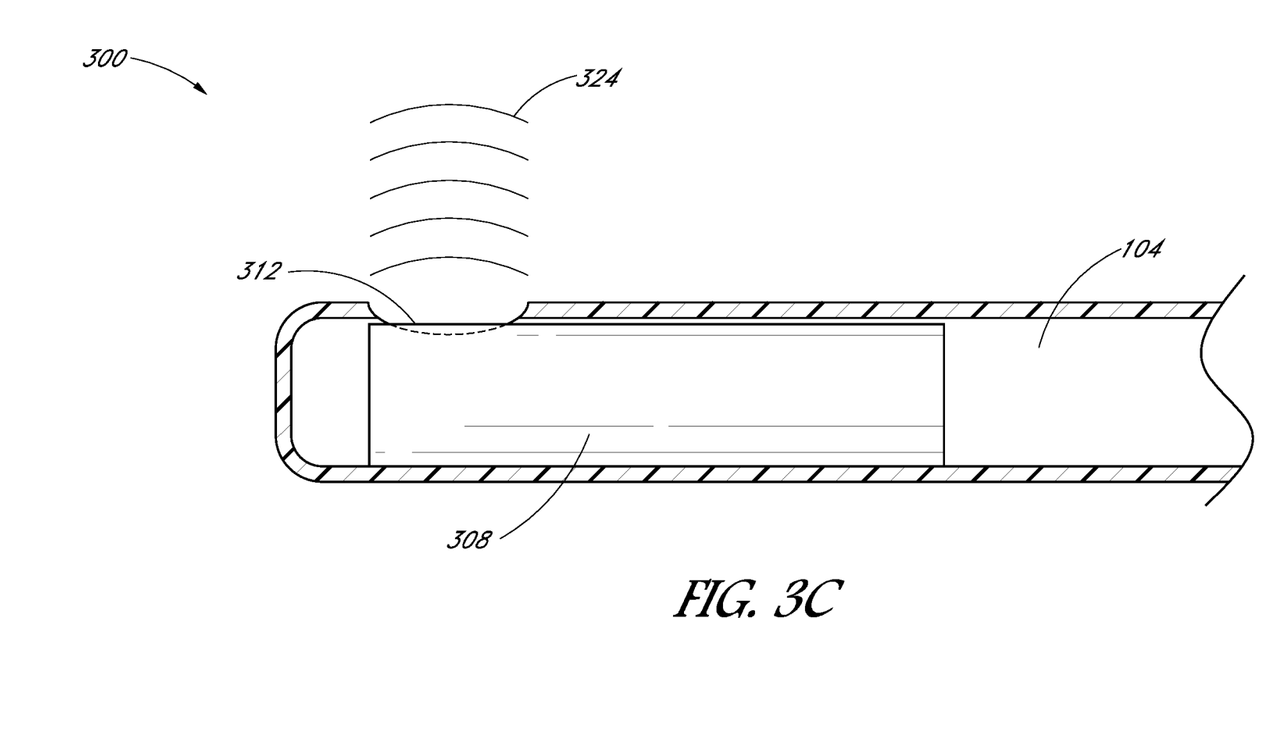

FIGS. 3A-C depict a miniaturized transducer 300 as may be employed in embodiments. In the embodiment shown, transducer 300 includes a housing 304, a backing 308, and at least one piezoelectric element 312. In the embodiment shown, backing 308 meets housing 304 at surface 316 having an angle relative to longitudinal axis 320. In the embodiment shown, the angle of surface 316 is a 45 degree angle relative to longitudinal axis 320 but other suitable angles may be used. In the embodiment shown, backing 308 extends longitudinally along longitudinal axis 320. In some embodiments, miniaturized transducer 300 may be disposed inside an insertion device such as insertion device 104 comprising cannula 108. In the embodiment shown, backing 308 extends in a direction perpendicular to a direction ultrasound waves/signals 324 are emitted via piezoelectric element 312. In the embodiment shown, the direction ultrasound waves/signals 324 are emitted is parallel to a normal 328 of piezoelectric element 312. In this configuration, backing 308 provides adequate dampening material to reduce the signal to noise ratio of the ultrasound waves to a suitable level that enables accurate ultrasonic imaging. In the embodiment shown, ultrasound waves 324 can be emitted along longitudinal axis 320 such as by ultrasound transmission line 144. Ultrasound waves 324 travel through backing 308, contact surface 316 at a 45-degree angle, are reflected from surface 316 in a direction perpendicular to longitudinal axis 320, and contact piezoelectric element 312 to be emitted outside of the transducer. In the embodiment shown, vibrations can return from tissue and return to contact and/or pass through piezoelectric element 312. In the embodiment shown, the sounds waves corresponding to the vibrations can be reflected from surface 316 in a direction parallel to longitudinal axis 320 and can be monitored/read by a data acquisition system.

Figure 4A:
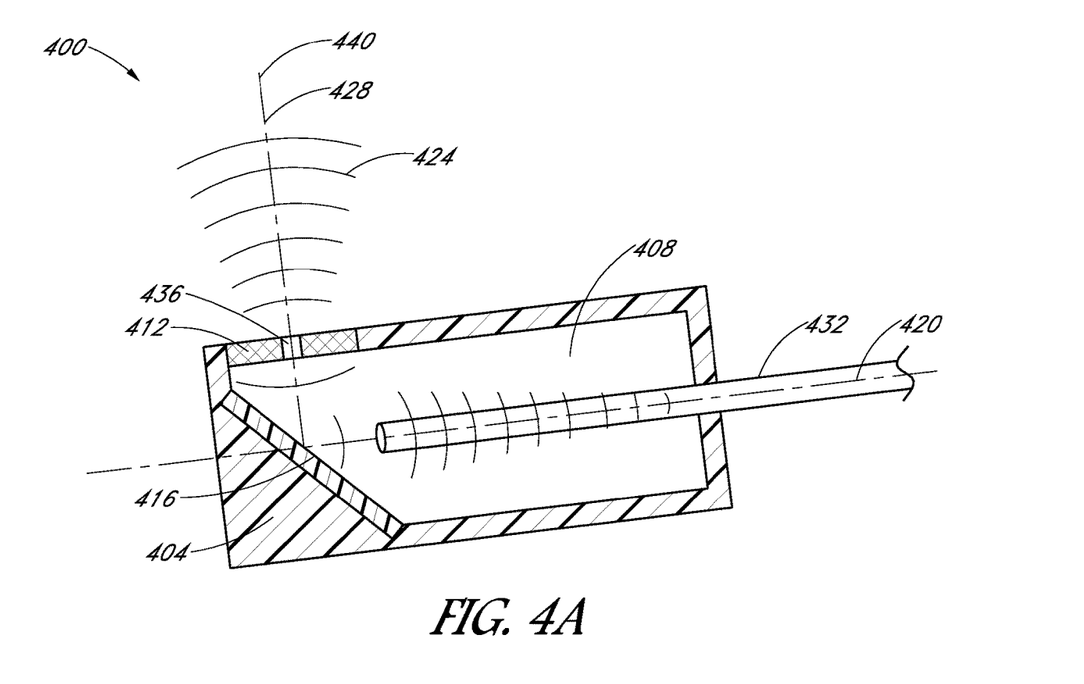
FIGS. 4A-4C depict a miniaturized transducer as may be employed or modified in embodiments.
Figure 4B:
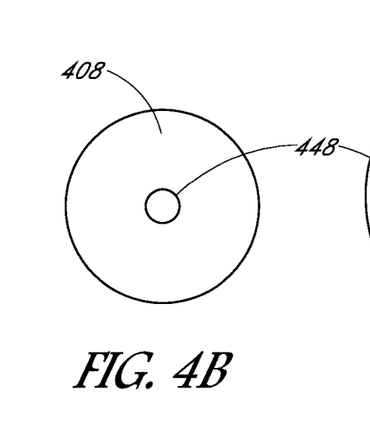
Figure 4C:
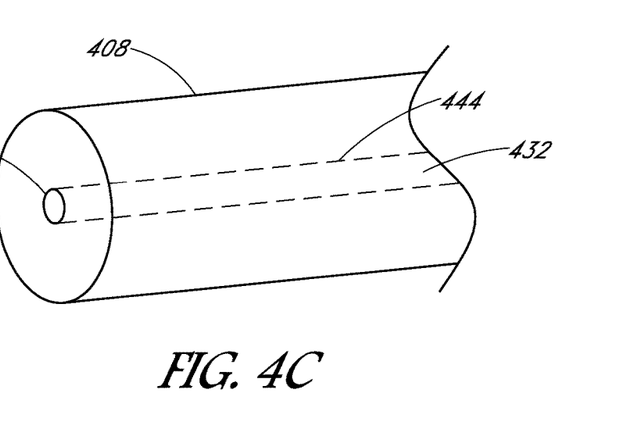

FIGS. 4A-C depict a miniaturized transducer 400 as may be employed in embodiments. In some embodiments, such as that shown in FIG. 1C, it is desirable to provide both ultrasonic and photoacoustic imaging capability. Transducer 400 includes a housing 404, a backing 408, and at least one piezoelectric element 412 and backing 408 meets housing 404 at surface 416 having an angle relative to longitudinal axis 420. In the embodiment shown, the angle of surface 416 is a 45-degree angle relative to longitudinal axis 420 but other suitable angles may be used. In some embodiments, surface 416 may be comprised of a material suitable to reflect both ultrasound waves and light waves. In some embodiments, surface 416 can be a mirror. This configuration is similar to that shown in FIGS. 3A-C and enables ultrasound waves 424 to be emitted by transducer 400. For photoacoustic imaging, light waves of a particular wavelength can also be emitted by transducer 400 to contact body tissue. The body tissue absorbs the light, heats up and expands, and emits vibrations that can be detected as sound waves. In the embodiment shown, light waves/signals 428 can be emitted such as by optical transmission line 432. In the embodiment shown, optical transmission line 432 extends longitudinally along longitudinal axis 420 and can be disposed inside an insertion device such as insertion device 104 comprising cannula 108. In the embodiment shown, optical transmission line 432 emits light waves 428 along longitudinal axis 420 which contact surface 416 at a 45 degree angle, and are reflected from surface 416 in a direction perpendicular to longitudinal axis 420. In the embodiment shown, piezoelectric element 412 comprises an aperture 436 disposed in piezoelectric element 412 that is configured to allow the reflected light waves 428 to pass through aperture 436 and be emitted from transducer 400. In the embodiment shown, the direction light waves/signals 428 are reflected from surface 416 is parallel to a normal 440 of piezoelectric element 412. In the embodiment shown, normal 440 passes through a center of aperture 436. In the embodiments shown, optical transmission line 432 can pass through a channel 444 disposed in backing 408 along longitudinal axis 420 and can enter and exit channel 444 via one or more apertures 448. In this way, both ultrasound waves 424 and light waves 428 can be reflected by surface 416 to contact and/or pass through piezoelectric element 412. In this way, both ultrasound waves 424 and light waves 428 can be emitted by transducer 400 in the same direction and through the same aperture, such as transducer aperture 132 disposed in a surface of cannula 108. In some embodiments, optical transmission unit 432 can be configured to emit light waves out of a different aperture of cannula 108. In the embodiment shown, vibrations from heated tissue can return to contact and/or pass through piezoelectric element 412. In the embodiment shown, the sounds waves corresponding to the tissue vibrations can be reflected from surface 416 in a direction parallel to longitudinal axis 420 and can be monitored/read by a data acquisition system. In this way, both ultrasound waves and photoacoustic waves can be collected to enable real time reconstruction of the waves to construct images by a data acquisition and/or computing system in some embodiments.

In an exemplary operation of the described embodiments, insertion device 104 may be inserted into an organ (e.g., a uterus) of a patient via a biological orifice (e.g., vaginal opening, cervical opening). In some embodiments, when insertion device 104 is positioned in the organ, other components of system 100 such as an actuator when present, may remain positioned externally relative to the organ and/or the patient. After insertion device 104 is disposed in the organ, an actuator (e.g., via signals from a position control device) may control movement of the insertion device. For example, in this embodiment, an actuator may move insertion device 104 proximate to an area of interest in the organ, whereby the insertion device is at a starting position and ready to begin an imaging procedure. In other embodiments, as noted above, insertion device 104 can be manipulated by hand. Next, the following steps may be performed and/or repeated (e.g., with alterations) until the area of interest in the organ has been appropriately imaged.

In the embodiment shown, an ultrasound pulser-receiver may transmit a signal to transducer 300, 400 via an ultrasound transmission line similar to ultrasound transmission line 144. Next, in the embodiment shown, ultrasound signals 324, 424 contact surface 326, 416 and are reflected radially outward relative to longitudinal axis 320, 420 to contact and/or pass through piezoelectric element 312, 412. Next, in the embodiment shown, transducer 300, 400 receives an ultrasound echo signal (e.g., an ultrasound signal reflected by the tissue of the organ). In the embodiment shown, transducer 300, 400 may convert the ultrasound echo signal into a signal transmittable via the ultrasound transmission line to an ultrasound pulser/receiver. Next, in some embodiments, the signal may be amplified by an amplifier and the amplified signal may be transmitted to a data acquisition device, which may transmit image data to a computer. In some embodiments, a computer may render on a display a three-dimensional image in real time based on the ultrasound echo signal received by ultrasound transducer.

In embodiments having photoacoustic imaging capability such as that depicted in FIGS. 4A-C, a trigger may (e.g., by user input via a computer) direct a laser to emit a light signal 428 (e.g., a laser beam) into a fiber alignment stage, which can thereby transmit light signal 428 through optical transmission line 432 toward reflective surface 416. Thereafter, light signal 428 reflects off of reflective surface 416 and is directed radially outward relative to longitudinal axis 420. As shown, in FIG. 4A, light signal 428 is reflected off of reflective surface 416 in a direction substantially perpendicular to longitudinal axis 420 and/or substantially parallel to ultrasound signal 424. In the depicted embodiment, light signal 428 may induce a photoacoustic effect in the tissue of the organ exposed to the light signal. In this embodiment, heat from light signal 428 may be absorbed by the tissue and may cause the tissue to expand. In turn, the heat-related tissue expansion due to exposure to light signal 428 may result in a photoacoustic signal (e.g., a soundwave) being emitted from the tissue. In this embodiment, transducer 400 may receive a photoacoustic signal and convert the photoacoustic signal into a signal transmittable via an ultrasound transmission line similar to ultrasound transmission line 144. Thereafter, as discussed herein, the signal may be ultimately transmitted to a computer via an ultrasound pulser-receiver, an amplifier, and/or a data acquisition device. In some embodiments, a computer may reconstruct and/or update a rendered three-dimensional image on a display in real time based on a photoacoustic signal and/or an ultrasound echo signal. More particularly, in some embodiments, a three-dimensional image rendered by a computer may comprise one or more overlaid images providing a more comprehensive view of the tissue. For example, in some embodiments, the overlaid images may include an optical image (e.g., for insertion device guidance and surface characterization of tissue, such as, of the endometrium), an ultrasound image (e.g., for characterizing tissue density, such as, within the endometrium and myometrium along with thickness of the endometrial stripe), and a photoacoustic image (e.g., for vasculature mapping). In some embodiments, the overlaid images may aid in the identification of potential lesions or other problem areas in the tissue.

In some embodiments, transducer 300, 400 may be configured to capture three-dimensional images while insertion device 104 moves axially and/or rotationally relative to longitudinal axis 124. For example, in some embodiments, a position control device may cause a rotary motor to rotate insertion device 104 in a first direction such that ultrasound signal 324, 424 and light signal 428 are repeatedly emitted (e.g., at a predetermined frequency) in controlled pulses until at least a full revolution of the insertion device is achieved and a corresponding three-dimensional image is captured by the system as described herein. In some embodiments, after at least the full revolution is achieved, a position control device may direct a linear actuator to move insertion device 104 axially such that transducer 300, 400 may capture images of additional tissue. In some embodiments, after insertion device 104 is axially moved by a linear actuator, a rotary motor may rotate the insertion device in a second direction (e.g., an opposite direction relative to a first direction) and transducer 300, 400 may capture additional three-dimensional images as described herein. In some embodiments, a position control device may direct an actuator to rotate an insertion member (e.g., 104) in a first direction and/or a second direction before and/or after moving the insertion member axially. Thereafter, axial and/or rotational movement of insertion device 104 may be repeated until a comprehensive three-dimensional image of the tissue, organ, vasculature, contrast agents, etc. of the target area is captured. In this embodiment, a data acquisition device and/or a computer may store spatial coordinates of the data which make up the three-dimensional image on a display. In some embodiments, using the spatial coordinates from the imaging data corresponding to the tissue of interest identified by a physician-guided software program, a position control device may direct an actuator to move and orient insertion member 104 relative to the tissue such that a biopsy device may collect a biopsy sample of the tissue of interest. Thereafter, insertion device 104 may be removed from the organ and the tissue sample may be examined.

In these ways and others, areas of interest in the organ may be imaged in real time by transducer 300, 400 and controlled biopsy samples may be collected from the areas of interest by the system based on the real time images.

Although the embodiments described herein are useful in uterine applications, they can be used in other applications, both biomedical or otherwise. For example, the described embodiments can be used for a uterine cancer application as described above, or can be used for underwater imaging. The disclosed embodiments can be used for any application or in any environment where a mini-transducer is necessary and/or desirable to maintain or improve functionality while limiting the footprint of the transducer.

The above specification and examples provide an illustrative description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A medical apparatus comprising:
   a flexible tubular elongated probe having a length, a first end, a second end, and a channel between the first end and the second end, the channel disposed in a longitudinal direction along a longitudinal axis of the length of the probe; and
   a transducer disposed within the channel at the first end of the probe, the transducer comprising:
   an external housing,
   a backing within the housing,
   at least one reflective planar angled surface within the housing, and
   a piezoelectric element supported by the external housing, the piezoelectric element positioned to receive a signal wave and transfer the received signal wave into the housing and towards the at least one reflective planar angled surface within the housing, the at least one reflective planar angled surface positioned on the longitudinal axis to reflect a signal from the piezoelectric element in the longitudinal direction along the longitudinal axis of the probe.

2. The medical apparatus of claim 1, where the piezoelectric element is disposed within an aperture disposed in an external surface of the probe.

3. The medical apparatus of claim 1, where a sensor of the piezoelectric element is parallel to the longitudinal axis of the probe.

4. The medical apparatus of claim 1, where the probe includes an ultrasound transmission line configured to extend within the channel in the longitudinal direction along the longitudinal axis of the probe between the transducer and the second end of the device.

5. The medical apparatus of claim 1, where the reflective planar angled surface is disposed at a 45-degree angle relative to the longitudinal axis of the probe.

6. The medical apparatus of claim 1, where the reflective planar angled surface is disposed at a 45-degree angle relative to the normal of the piezoelectric element.

7. The medical apparatus of claim 1, where the reflective planar angled surface is integrated along an internal surface of the housing.

8. The medical apparatus of claim 1, where the reflective planar angled surface is disposed at a 15 degree angle relative to the longitudinal axis of the probe or where the reflective planar angled surface is disposed at a 30 degree angle relative to the longitudinal axis of the probe or where the reflective planar angled surface is disposed at a 60 degree angle relative to the longitudinal axis of the probe or where the reflective planar angled surface is disposed at a 75 degree angle relative to the longitudinal axis of the probe.

9. The medical apparatus of claim 1, where the reflective planar angled surface is disposed at a 15 degree angle relative to the normal of the piezoelectric element or where the reflective planar angled surface is disposed at a 30 degree angle relative to the normal of the piezoelectric element or where the reflective planar angled surface is disposed at a 60 degree angle relative to the normal of the piezoelectric element or where the reflective planar angled surface is disposed at a 75 degree angle relative to the normal of the piezoelectric element.

* * * * *